(12) United States Patent
Wands et al.

(10) Patent No.: US 7,122,541 B2
(45) Date of Patent: *Oct. 17, 2006

(54) METHODS OF INHIBITING METASTASES

(75) Inventors: Jack R. Wands, Waban, MA (US); Rolf I. Carlson, Boston, MA (US); Paul Maggio, Cranston, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/873,802

(22) Filed: Jun. 21, 2004

(65) Prior Publication Data

US 2005/0032785 A1    Feb. 10, 2005

Related U.S. Application Data

(63) Continuation of application No. 10/262,778, filed on Oct. 1, 2002, now Pat. No. 6,753,328.

(60) Provisional application No. 60/326,288, filed on Oct. 1, 2001.

(51) Int. Cl.
*A61K 31/54*    (2006.01)

(52) U.S. Cl. .............. 514/222.5; 514/893; 604/890.1; 604/891.1; 604/892; 604/506; 604/507; 604/508; 604/510

(58) Field of Classification Search ................ 604/27, 604/96, 43, 506, 510; 514/222.5, 893
See application file for complete search history.

(56) References Cited

U.S. PATENT DOCUMENTS

| | | | |
|---|---|---|---|
| 6,287,273 B1 * | 9/2001 | Allers et al. .................. 604/27 |
| 6,429,224 B1 * | 8/2002 | Calabresi et al. ........... 514/422 |
| 6,521,616 B1 * | 2/2003 | Calabresi et al. ........ 514/222.5 |
| 6,753,328 B1 * | 6/2004 | Wands et al. ............ 514/222.5 |

* cited by examiner

*Primary Examiner*—Ardin H. Marschel
*Assistant Examiner*—Shirley V. Gembeh
(74) *Attorney, Agent, or Firm*—Mintz, Levin, Cohn, Ferris, Glovsky and Popeo, P.C.; Ingrid A. Beattie

(57) ABSTRACT

The invention relates to methods for preventing and treating disseminating cancers. Inhibition metastases of a primary tumor to a liver tissue is carried out by directly contacting a liver tissue with Taurolidine.

16 Claims, 12 Drawing Sheets

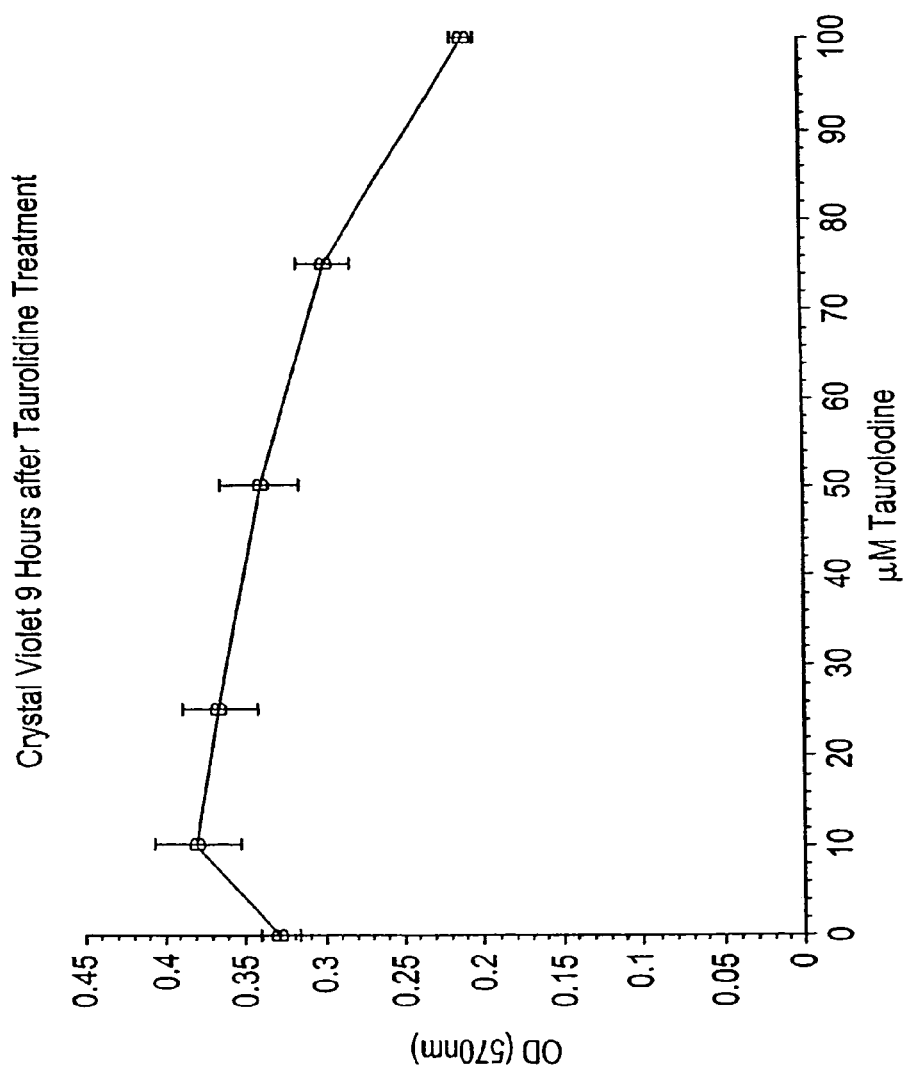

G1: 54%
S: 25%
G2/M: 21%

G1: 58%
S: 23%
G2/M: 19%

G1: 50%
S: 25%
G2/M: 25%

FIG. 4A  FIG. 4B  FIG. 4C
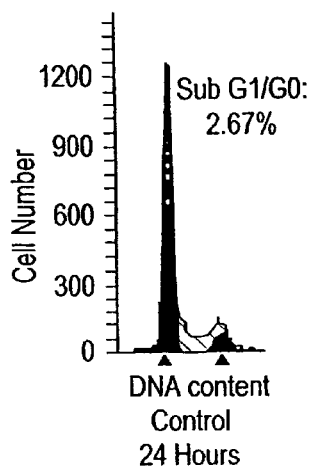
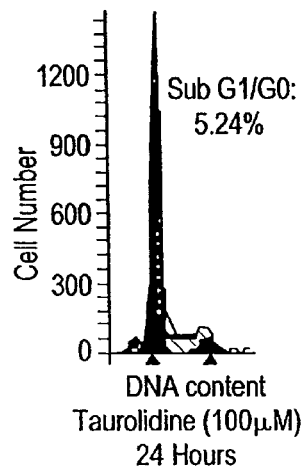
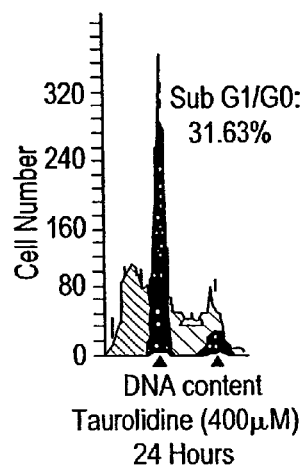
FIG. 4D
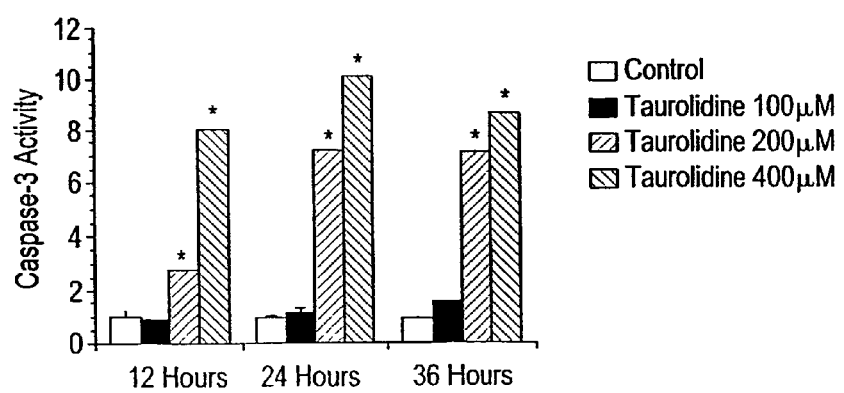

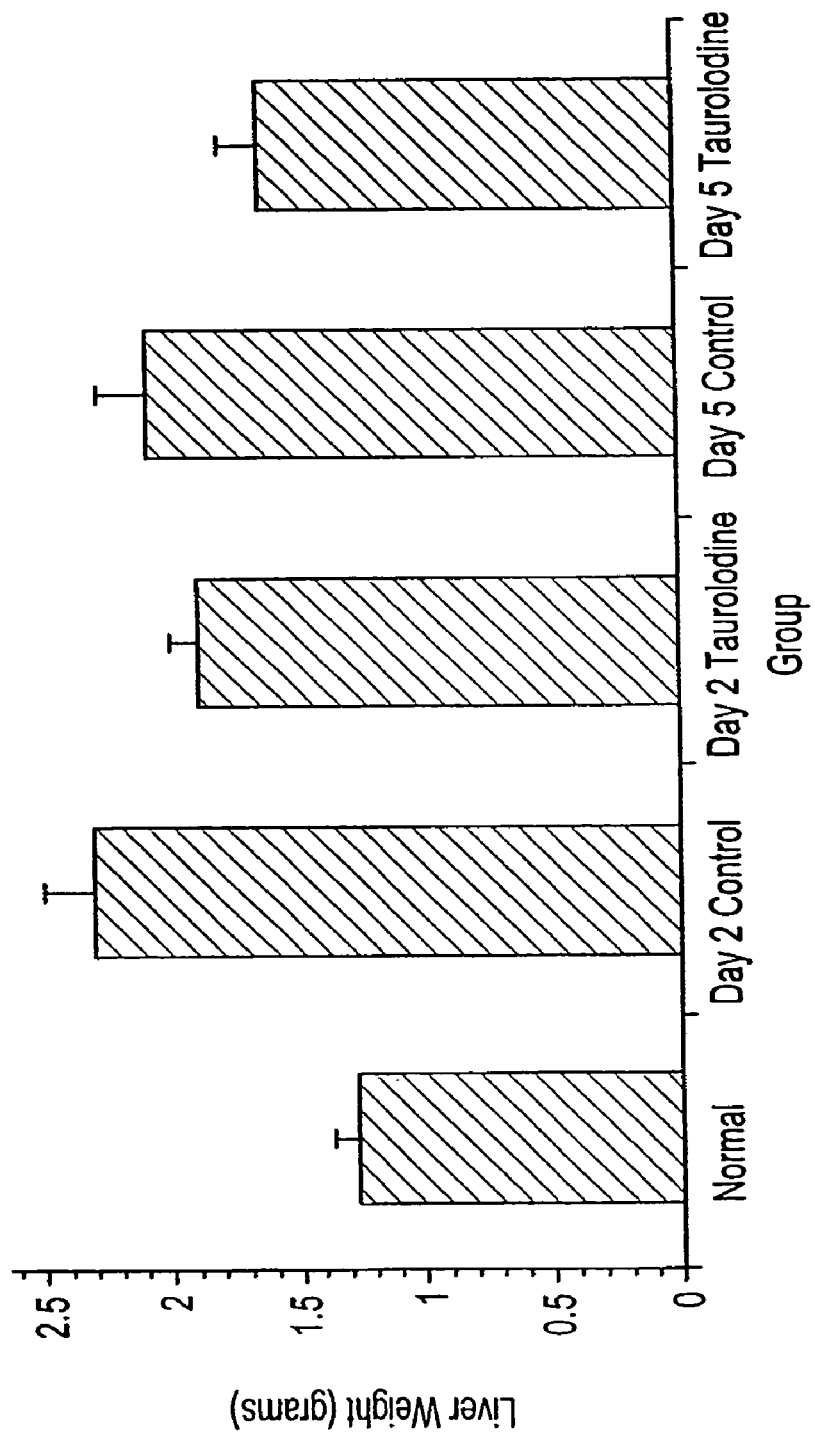

METHODS OF INHIBITING METASTASES

PRIORITY INFORMATION

This application is a continuation of U.S. patent application Ser. No. 10/262,778, filed Oct. 1, 2002 now U.S. Pat. No. 6,753,328, which claims priority to provisional patent application U.S. Ser. No. 60/326,288, filed on Oct. 1, 2001, the entire contents of which is hereby incorporated by reference.

STATEMENT AS TO FEDERALLY SPONSORED RESEARCH

This invention was made with U.S. government support under National Institutes of Health grant number CA-35711 and AA002666. The government has certain rights in the invention.

BACKGROUND OF THE INVENTION

The invention relates to cancer therapy.

Colorectal cancer is the third most common malignancy in men and women in the United States and is the second leading cause of cancer deaths. It is responsible for an estimated 56,700 deaths in 2001. Approximately 60 percent of those patients diagnosed with colorectal cancer will develop hepatic metastases for which the therapeutic gold standard remains hepatic resection. Despite surgical treatment, the majority of patients after liver resection will develop recurrences and of these recurrences, approximately fifty percent will be within the liver.

SUMMARY OF THE INVENTION

The invention features methods for preventing and inhibiting the spread of disseminating cancers. For example, a method of inhibiting metastases of a primary tumor to a liver tissue is carried out by directly contacting a liver tissue with Taurolidine. Preferably, the primary tumor is not a liver tumor. The primary tumor is in an organ of the peritoneal cavity. Advantages of the invention include reduction in the need for hepatic resection.

The method also includes a step of identifying an individual who is at risk of developing a metastatic liver tumor. For example, the individual is identified as suffering from a colorectal tumor or another tumor such as a lung tumor, breast tumor, kidney tumor, colon tumor, esophageal tumor, testicular tumor, pancreatic tumor, melanoma, or choriocarcinoma. Patients, who have been diagnosed with a class of tumors which commonly metastasize to the liver, are treated with Taurolidine.

The individual to be treated is a mammal such as a human patient. However, the methods are applicable to veterinary use, e.g., for the treatment of tumor metastases in pets such as dogs or cats or in livestock.

To treat or prevent metastatic disease of the liver, liver tissue is isolated from systemic circulation prior to contacting it with Taurolidine. For example, the liver is perfused with Taurolidine in situ. Liver blood circulation is essentially isolated from systemic blood circulation while liver tissue is contacted with the drug. Perfusion is performed prior to or after excision of a primary tumor. Perfusion is also carried out in conjunction with an abdominal surgery, e.g., when the abdominal cavity is surgically accessible during removal of a tumor. Other methods of administration include contacting the liver over time using in-dwelling catheter. The therapeutic methods includes peritoneal or intravenous (or other systemic) administration. Alternatively, the method does not include peritoneal or intravenous administration of Taurolidine. Drug is infused into the liver directly via the hepatic artery (pre-op; post-op; and/or during an operation to surgically remove a tumor).

Drug is administered intraperitoneally and/or intravenously before, during or after surgical removal of a tumor mass. For example, Taurolidine is administered 1, 2, 3, 4, 5, 10 or more days prior surgery. Local tissues in the area of resection are optionally bathed in a Taurolidine solution following removal of a tumor mass. Following surgery and to inhibit secondary tumor formation, drug is administered for several days (1–7 days), to weeks, and months after removal of a tumor.

Taurolidine compositions are administered at a dose that is therapeutically effective to prevent or inhibit tumor cell adherence. The term "therapeutically effective amount" as used herein means that the amount of a compound(s) or pharmaceutical composition elicits a beneficial biological or medicinal response in a tissue, system, animal or human. For example, a therapeutically effective amount of a Taurolidine reduces the number of metastatic foci in the liver tissue. Therapeutic effectiveness is also indicated by a reduction in the amount of a tumor associated antigen, e.g., carcinoembryonic antigen (CEA) or prostate specific antigen (PSA), following treatment. Taurolidine is administered alone or in combination with one or more other anti-cancer compositions. Preferably, the drug is administered at a dose that inhibits cell adherence but is not cytotoxic. The drug is administered at a doses that increase caspase (e.g., caspase-3) activity in a cell. For example, the dose induces caspase-mediated apoptosis of a cell which has been contacted with Taurolidine.

Therapeutic compositions are isolated or purified. An "isolated" or "purified" protein or biologically active portion thereof is substantially free of cellular material or other contaminating proteins from the cell or tissue source from which it is derived, or substantially free from chemical precursors or other chemicals when chemically synthesized. Preferably, a preparation of a therapeutic compound, e.g, Taurolidine, is at least 75%, more preferably 80%, more preferably 85%, more preferably 90%, more preferably 95%, more preferably 98%, and most preferably 99 or 100% of the dry weight of the preparation.

Other features, objects, and advantages of the invention will be apparent from the description and from the claims. Unless defined otherwise, all technical and scientific terms used herein have the same meaning as commonly understood by one of ordinary skill in the art to which this invention belongs. All patents and publications cited in this specification are incorporated by reference.

BRIEF DESCRIPTION OF THE DRAWINGS

In FIG. 1A, LS-180 cells were treated with 10, 25, 50, 75, and 100 μm concentrations of Taurolidine in a 96-well microtiter plate. A 100 μm concentration of Taurolidine produced a 40–50% decrease by MTT assay, which was present as early as 9 hours after Taurolidine exposure. In FIG. 1B, LS-180 cells, were incubated with 100, 200, and 400-μM concentrations of Taurolidine. In FIG. 1B, cell number was assessed using WST-8, a tetrazolium salt, at 12, 24 and 36 hours. Results are presented as the mean percent difference from untreated cells (control), ±SE.

FIGS. 2A–B are line graphs showing the effect of Taurolidine on LS-180 cell viability by crystal violet assay. In FIG. 2A, cells were treated with 10, 25, 50, 75, and 100 µm concentrations of Taurolidine, and cell viability was measured in a 96-well microtiter plate. In FIG. 2B, cells were treated with 100, 200, and 400-µM concentrations of Taurolidine. The crystal violet assay demonstrated a corresponding decrease in cell viability compared to the MTT assay, representing a decrease in adherent cell number. The data shows that Taurolidine causes loss of cell adherence. Culture medium and nonadherent cells were removed prior to fixation and staining with crystal violet. Results are presented as the mean percent difference from untreated cells (control), SE.

FIG. 3A shows control cells (cell in the absence of Taurolidine); FIG. 3B shows cells treated with 50 µm Taurolidine; and FIG. 3C shows cells treated with 100 µm Taurolidine. Flow cytometry using the DNA fluorochrome propidium iodide failed to demonstrate a sub-GI peak, and demonstrated no significant change in cell cycle progression. 10,000 events were collected.

FIGS. 4A–D are histograms showing that Taurolidine induces apoptosis in human colon cancer cells. In FIGS. 4A–C, LS-180 cells were treated with 100, 200, and 400 µM concentrations of Taurolidine. After 24 hours the cells were harvested by trypsinization, labeled with propidium iodide, and their DNA content was measured by flow cytometry. The percentage of subdiploid DNA content, representing DNA degradation in apoptotic cells, is shown. FIG. 4D is a bar graph showing that Taurolidine produces a dose-dependent increase caspase-3 activity. LS-180 cells were treated with 100, 200, and 400 -µM concentrations of Taurolidine and harvested by trypsinization at 12, 24, and 36 hours. Caspase-3 activity was assessed by its ability to cleave the DEVD-pNA colorimetric substrate. Data shown represents the mean activity ±SD and was performed in three separate experiments. *P<0.001, Bonferroni/Dunn test.

FIG. 6B shows that loss of cell adherence is not affected by caspase inhibition. The corresponding crystal violet assay for Taurolidine-treated LS-180 cells after caspase inhibition with 50-uM Z-VAD-fmk is shown. Culture medium and nonadherent cells were removed prior to fixation and staining with crystal violet. Results are presented as the mean percent difference from untreated cells in an equivalent dilution of DMSO (control), ±SE. To confirm caspase inhibition by Z-VAD-fmk caspase-3 activity was assessed using a DEVD-pNA colorimetric substrate (FIG. 6C). There was no significant increase in caspase-3 activity in cells treated with Z-VAD-fmk at all studied concentrations of Taurolidine compared to untreated LS-180 cells (control). Cells treated with a 400 µM concentration of Taurolidine without caspase inhibition served as a positive control. All cells were treated with an equivalent concentration of DMSO. Data shown represents the mean activity±SD and was performed in three separate experiments.

FIG. 10 is a bar graph showing average liver weights of study animals after completing 3 weeks of Taurolidine versus control animals. Taurolidine treated animals demonstrated an 18–22% reduction in the 2 and 5 day groups respectively, representative of decreased tumor burden in the treated animals.

DETAILED DESCRIPTION OF THE INVENTION

Figure 1A:
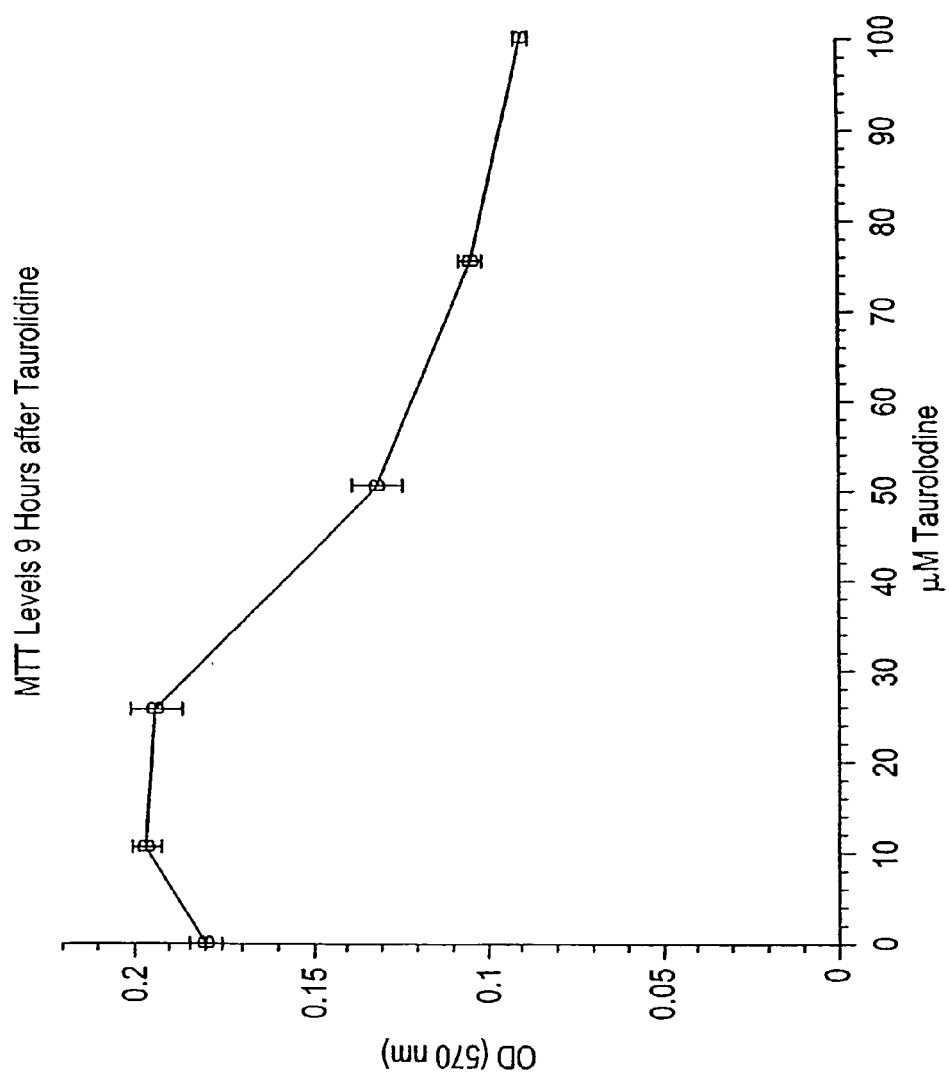
FIGS. 1A–B are line graphs showing the effect of Taurolidine on LS-180 cell proliferation.
Figure 1B:
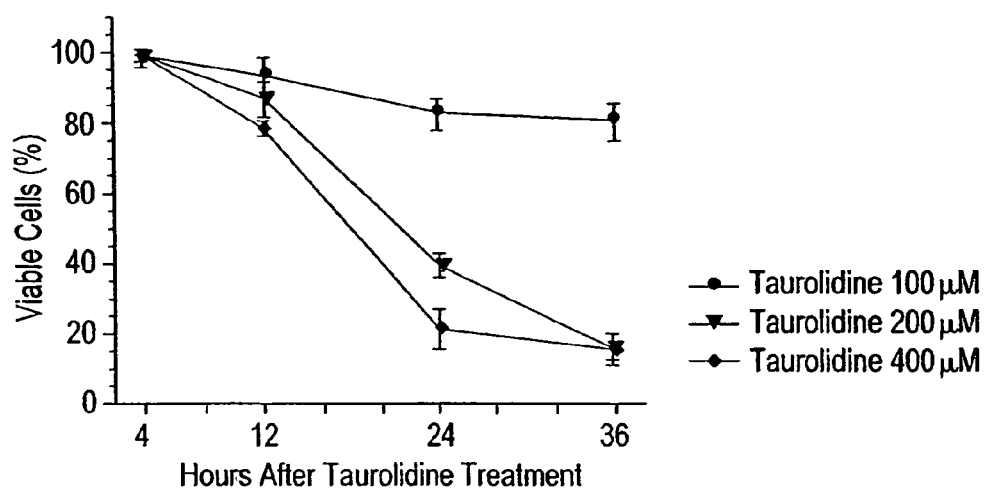
Figure 2B:
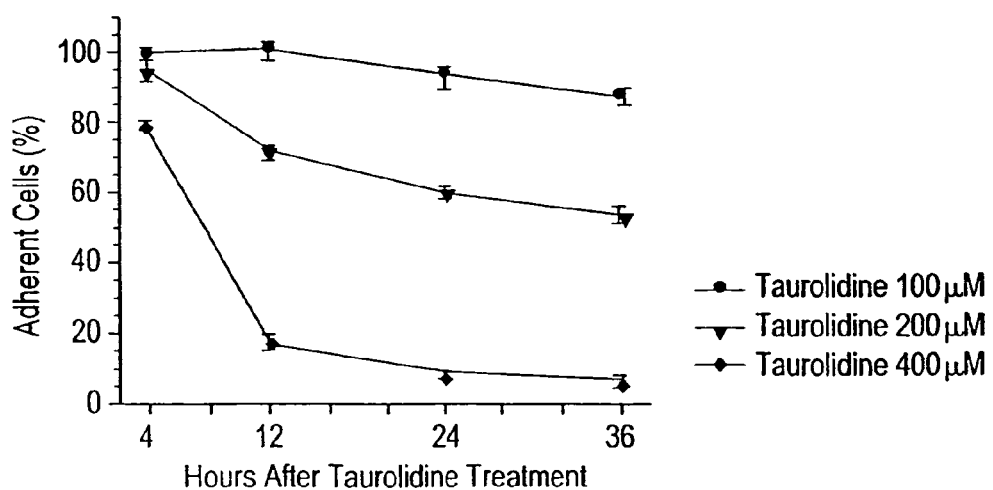
Figure 3A:
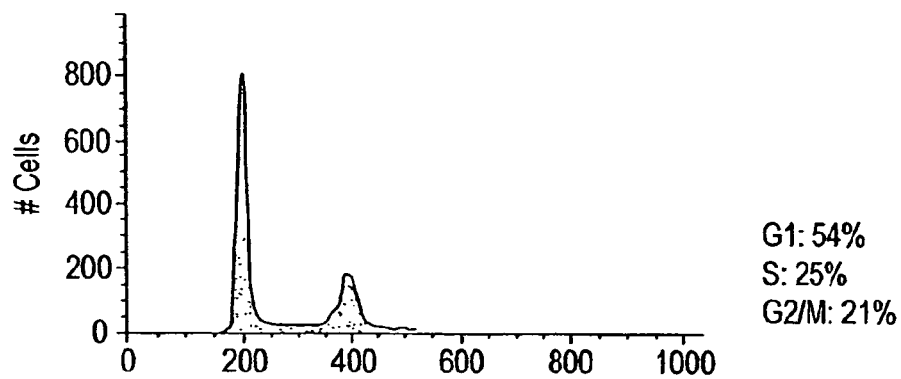
FIGS. 3A–C are histograms showing the results of a flow cytometry analysis performed on LS-180 cells treated with 50 and 100 µm concentrations of Taurolidine for 24 hours.
Figure 3B:
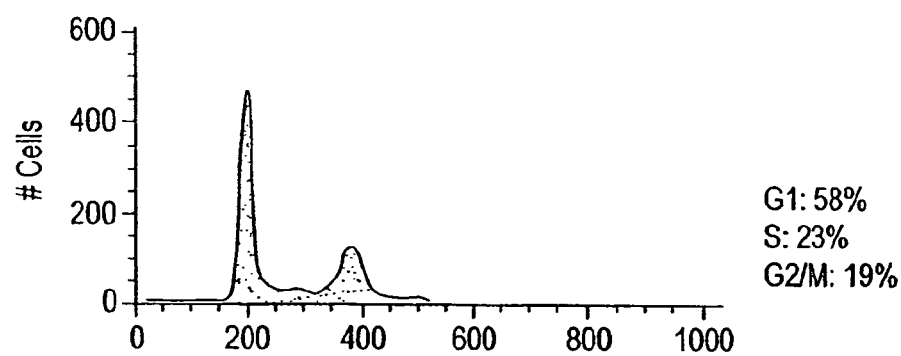
Figure 3C:
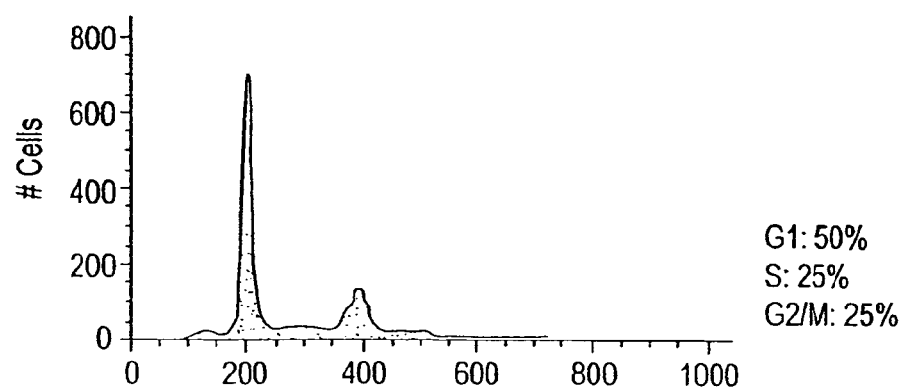
Figure 5:
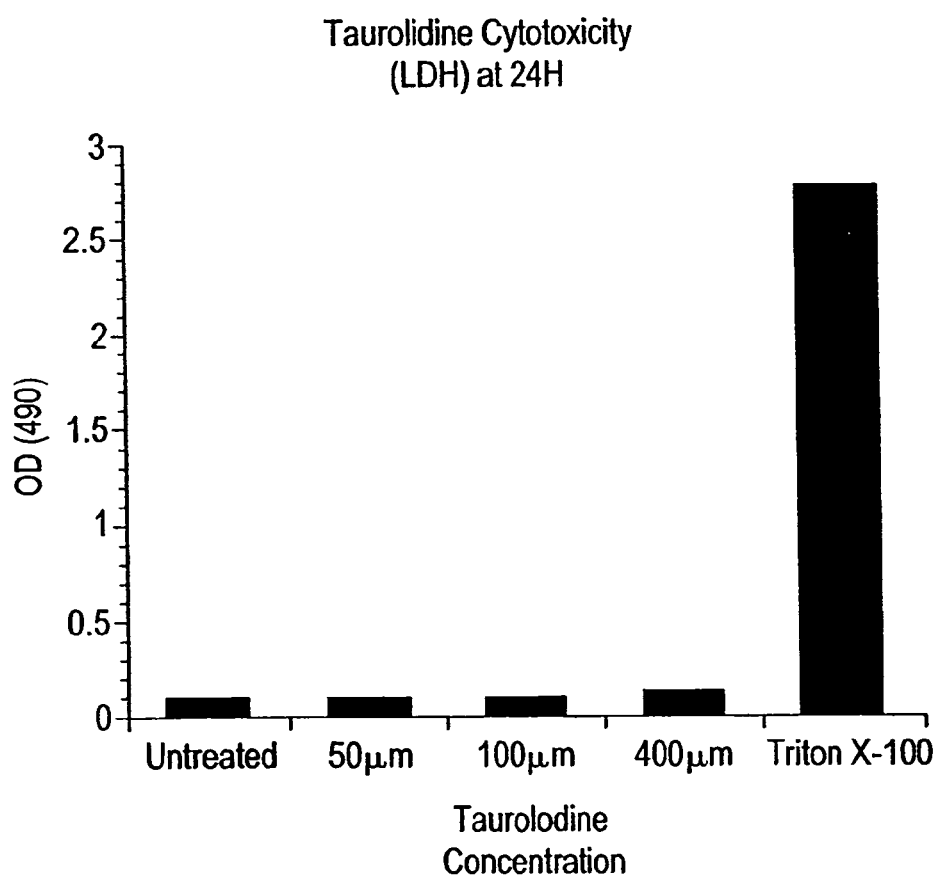
FIG. 5 is a bar graph showing cytotoxicity produced in LS-180 cells treated with Taurolidine as measured by LDH release. LS-180 cells were treated with 50, 100 and 400 µm concentrations of Taurolidine for 24 hours. Triton X-100 cells produced a maximal LDH release (high control, see materials and methods). Taurolidine, even at a 400 µm concentration, produced very little cytotoxicity. The percent cytotoxicity for the 50, 100, and 400 µm groups were –0.07%, 0.15%, and 1.58% respectively.
Figure 6A:
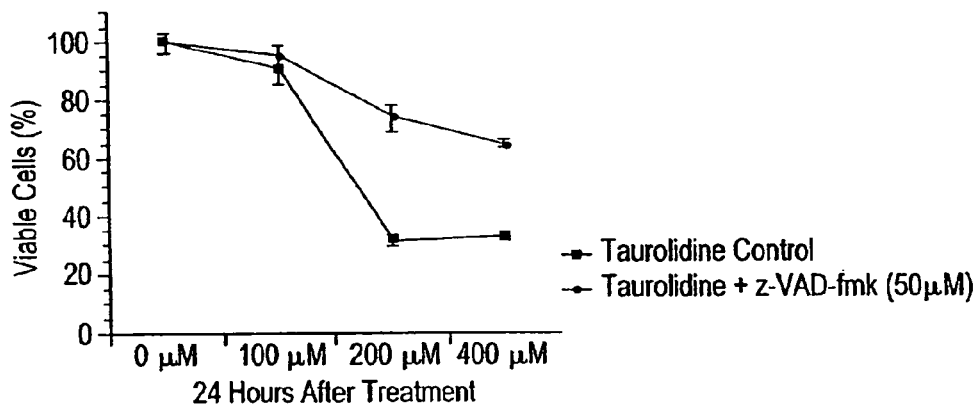
FIGS. 6A–B are line graphs and FIG. 6C is a bar graph showing that the apoptotic effects of Taurolidine are mediated through caspase activation. The data in FIG. 6A was generated using LS-180 cells. The cells were treated with a 50-EM concentration of the inhibitory peptide Z-VAD-fmk prior to treatment with Taurolidine. LS-180 cells were then incubated with 100, 200, and 400-EM concentrations of Taurolidine and cell number was assessed using WST-8, a tetrazolium salt, at 12, 24 and 36 hours. Results are presented as the mean percent difference from untreated cells in an equal dilution of DMSO (control), SE.
Figure 6B:
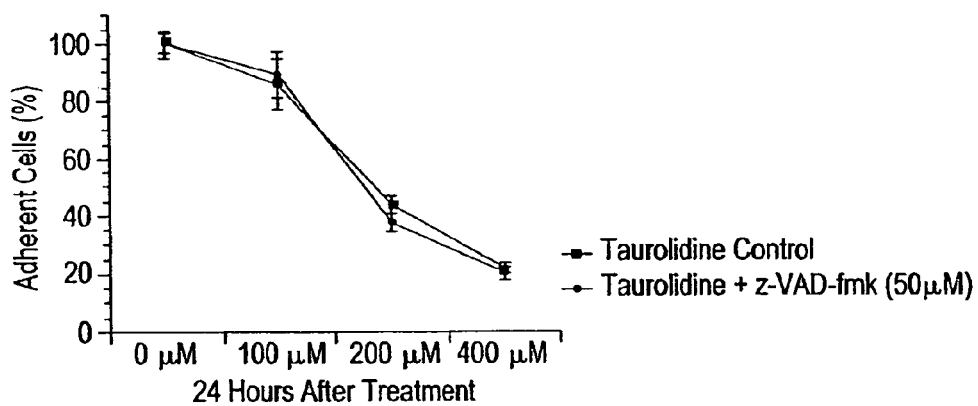
Figure 6C:
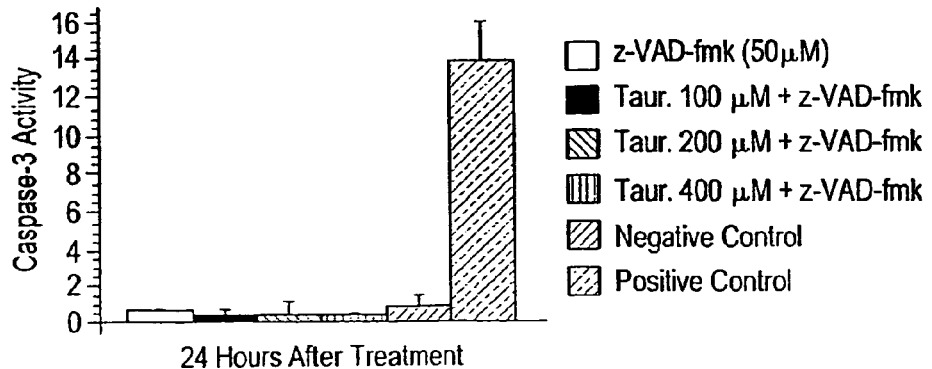

Taurolidine (bis(1,1-dioxoperhydro-1,2,4-thiadiazinyl-4) methane), a derivative of the amino acid taurine, has been used as an antibiotic in treating local and systemic infections. Taurolidine compositions and formulations are known in the art, e.g., as described in U.S. Pat. No. 5,210,083.

Taurolidine was used as a local agent as well as administered systemically for established tumors in a liver metastases model using the human colon cancer cell line, LS-180. In this established model to produce liver metastases, nude mice underwent splenic injection of tumor cells followed by splenectomy. Beginning post injection days 2 or 5 when micro metastatic disease was widespread within the liver, daily treatment of mice was initiated with intraperitoneal Taurolidine. Treatment with Taurolidine resulted in a dramatic reduction of tumor burden represented by a decrease in gross tumor as well as serum CEA levels.

In vitro studies demonstrated a decreased number of adherent tumor cells after incubation with Taurolidine. This effect appears not to involve apoptosis or cytolysis.

Metastases of a Tumor to a Liver Tissue

The liver is a common site of metastatic cancers. For example, approximately half of patients with colorectal cancer develop hepatic metastases. The portal vein drains the abdominal viscera and is a conduit for metastases from tumors of primary tumors originating in other organs such as the colon and rectum, stomach, pancreas, biliary tree, small intestine, and breast. Other primary cancers, which often result in liver metastases include malignant melanoma, lung cancer, and lymphoma.

Methods of diagnosing an individual who is suffering from or is at risk of developing metastatic liver cancer are known in the art. For example, detection of pain in the abdomen, distention of the abdomen, jaundice, ascites, or an abnormal liver test (such as alkaline phosphatase or transaminases) in an individual, who has had a previous diagnosis of cancer, indicates that the individual is has or is at risk of developing a liver metastases. CT scan or ultrasound is also used to confirm a tumor in the peritoneal cavity. Diagnosis of any one of the above-listed primary tumors indicates that an individual is at risk of developing a metastatic tumor of the liver. Multiple metastatic lesions are often the case, but single metastases may be seen. Liver biopsy is optionally carried out to confirm metastatic liver cancer.

Surgical resection remains the first line treatment option of metastasic liver tumors. Since colorectal cancer spreads by metastasis solely or predominantly to the liver, preferentially or specifically targeting the liver is a preferred option for therapy.

The methods described herein are also useful to treat patients, who have been diagnosed with a liver tumor without a known primary site. In some cases, it may be impossible to distinguish metastatic liver disease from multicentric hepatocellular carcinoma. Such patients also derive therapeutic benefit from localized treatment of the liver with taurolidine.

At present, hepatic resection is and/or regional chemotherapy with cytotoxic agents such as floxuridine (FUDR) combined with hepatic resection are used to treat liver cancers. However, in some cases, the tumor is in an anatomical position in which resection is not possible. In those cases, the methods described herein may be the best or only therapeutic option. The methods described herein provide a non-toxic or minimally toxic alternative to standard methods of treating liver tumors.

Taurolidine Inhibits Development of Hepatic Metastases from Colon Cancer

Taurolidine was used as a systemic anti-tumor agent in an art-recognized animal model for established hepatic metastatic disease using a human colon cancer cell clone highly selected for a metastatic phenotype. Following splenic injection of tumor cells to seed the liver, established tumor metastases was histologically demonstrated as early as 5 days after tumor cell injection. Fifteen days after tumor injection, grossly visible metastatic lesions were observed as small punctate nodules within the liver parenchyma and on the capsule; after 24 days of observation, the liver had been almost completely replaced by colon cancer. Using a Taurolidine treatment regimen of 10-mg per day via IP injections for five consecutive days×3 weeks, a striking decrease in tumor burden compared to untreated control animals was observed. Anti-tumor effects were observed in mice beginning treatment 2 and 5 days post splenic injection of tumor but was more pronounced in the latter group, producing a 78% reduction in CEA levels compared to control animals. Taurolidine was well tolerated, resulting in no deaths of animals during the 3 weeks of therapy. Despite small residual nodules, Taurolidine strikingly inhibited the development and progression of liver metastases.

The data also support a role for Taurolidine as an antineoplastic agent. An 85% decrease in tumor cell viability was found by WST-8 and crystal violet assays, which occurred in a dose-dependent manner; significant anti-tumor effects were observed after 12 hours of treatment, and similar results were found with other types of tumor cells, e.g., using the human colon cancer cell line SKCO-1 and the human hepatoma cell lines Hep3B, HUH-7, HepG2 and FOCUS. Caspase-mediated apoptosis was identified as the mechanism by which Taurolidine exerts its anti-tumor activity. The induction of apoptosis is an important mechanism through which chemotherapeutic agents exert their cytotoxic effects on neoplastic cells.

Although there are many components in the apoptotic or programmed cell death pathway, key elements include DNA fragmentation by DNA endonucleases and activation of intracellular cysteine proteases (caspases). Taurolidine treatment of cells led to a dose dependent increase in a sub-diploid DNA peak, representing partial loss of DNA due to endogenous nucleases, as well as a dose dependent increase in caspase-3 activation. Significant suppression of Taurolidine-induced cytotoxicity was demonstrated using the broad-specificity caspase inhibitor Z-VAD-fmk.

Taurolidine treatment of cells led to a loss of adherence of LS-180 cells. Loss of cell adherence can occur as a downstream event in the apoptotic pathway, but in LS-180 cells treated with Taurolidine loss of cell adherence appears to be an early event, preceding the decrease in viable cells and independent of caspase activation. Therefore, loss of cell adherence appears to be a separate and distinct process from the caspase-mediated apoptotic effects of Taurolidine in LS-180 cells. Loss of cell adherence is one element of the antineoplastic effect of Taurolidine The data described herein generated using an art-recognized and realistic experimental model system indicates that Taurolidine is a surprisingly effective chemotherapeutic agent for the treatment of established hepatic metastases from colon cancer.

Local Administration to Liver Tissue

Liver tissue is directly contacted with Taurolidine to inhibit or prevent metastases. For example, a catheter system for perfusing the liver is used to introduce a Taurolidine solution into the hepatic artery. The catheter is transiently inserted or may be indwelling. One or more administrations of drug are delivered to the liver tissue. A single dose contains 50 µg, 1 mg, 1.5 mg, 2 mg, 4 mg, and up to 5 mg per infusion. The infusion volume is 0.1–5 ml, e.g., Taurolidine is delivered in a saline solution or another pharmaceutically acceptable excipient in a volume of 0.1 to 100 ml. For example, the taurolidine solution is administered in a volume of 1, 5, 10, 25, 50, 75, or 100 ml in a single administration. Repeated doses are administered as required to inhibit or prevent metastases of tumors into the liver. Liver tissue is monitored by methods known in the art, e.g., CT scan, ultrasound, or liver biopsy.

Methods for local delivery to the liver include surgically or non-surgically preferentially targeting and perfusing the liver. Methods and devices for liver perfusion are described in U.S. Pat. Nos. 5,069,662 and 6,287,273. For example, U.S. Pat. No. 6,287,273 describes a perfusion system, which is used to seal off the flow of blood above the liver, so that the organ is essentially isolated from the systemic circulation. Before starting the circulation in the bypass and the perfusion circuits, the circuits are filled with fluid in order to ensure that air does not enter the body through the circuits. Circulating the blood past the liver in the bypass circuit is achieved by pumping. The pressure of the venous blood in the lower parts of the body and in vena porta is not high enough to press the blood all the way to the outlet of the perfusion circuit. The procedure is used for preferential targeted local treatments of organs, which have well defined input and out blood vessels such as kidney, liver, pancreas, bladder and pelvis. Contact with surrounding tissues or sytemic circulation is minimal or absent. Therapeutic agents are introduce in the direction of naturally-occurring blood flow or by retrograde perfusion of the isolated organ. Retrograde perfusion is useful in cases when there is a considerable fraction of the blood flow, which does not enter or leave the organ through the main input and output blood vessels, e.g., in the liver.

Treatment proceeds for a period of time during which the body can manage without having the systemic blood circulation in contact with the perfused organ. After treatment, the perfusion circuit is filled with a fluid, e.g., blood, which was drawn from the patient at an earlier time or taken from another blood supply.

In another procedure for localized delivery of Taurolidine to the liver, the portal vein and hepatic artery are clamped using micro-aneurysm clips, and the portal vein is cannulated with a needle having an appropriate gauge proximal to the clip and the drug is injected. Hemostasis is achieved by direct pressure to the portal vein and topical thrombin application, as required. The clips are removed and the abdomen sutured, and the subjects are allowed to convalesce. Alternatively, the procedure is carried out with portal injection of the compound, in which case the portal vein is cannulated and the solution is pumped into the portal vein over a period of time.

Asanguineous perfusion of the liver is used to selectively perfuse the liver after excluding normal blood flow from the organ. The hepatic artery, portal vein, suprahepatic vena cava, right suprarenal vein and infrahepatic vena cava are clamped to achieve vascular exclusion of the liver. The portal vein is then cannulated with a catheter of appropriate gauge, while an incision is made in the anterior wall of the infrahepatic vena cava, with a suction cannula placed into the vena cava to collect outflow. Liver perfusion, is performed using a pump. Flow rate may range from 0.1 ml/min per gram of liver to 10 ml/min per gram of liver. After perfusion, the portal and caval vein incisions are sutured and the liver is revascularized.

Systemic Therapeutic Administration

Other standard methods of administration are also used. The drug is prepared in a form suitable for oral administration, such as a tablet or capsule. Typically, a pharmaceutically acceptable salt of the compound is combined with a carrier and moulded into a tablet. Suitable carriers include starch, sugars, dicalcium phosphate, calcium stearate, magnesium stearate. Such compositions optionally include one or more auxiliary substances, such as wetting agents, emulsifiers, preservatives, stabilizers, colouring additives, etc. The compositions are administered one or more times per day or week. An effective amount of such a pharmaceutical composition is an amount that provides a clinically significant effect against obesity. Such amounts depend, in part, on the particular condition to be treated, age, weight, and general health of the patient, and other factors evident to those skilled in the art. The compositions are administered in multiples dosages over time or administered as controlled release formulations suitable for implantation into a tissue such as the liver or other tissues. Implants are formulated to provide release of active compound over the desired period of time, which can be up to several years. Such biodegradable compositions for controlled release of encapsulated drugs are known in the art, e.g., as described in U.S. Pat. No. 6,277,413.

Taurolidine is administered alone or in combination with other drugs to treat cancer. For example, Taurolidine is administered prior to surgery, during surgery to excise, a tumor, of after surgery to inhibit metastases of tumor cells that may have dislodged from a primary tumor during the excision process. Radiation or other chemotherapeutic approaches are used in conjunction with Taurolidine treatment.

The compositions are administered per os, orally, parenterally (including subcutaneous injections, intravenous, intramuscular, intrastemal injection or infusion techniques), or rectally, in dosage unit formulations containing conventional non-toxic pharmaceutically acceptable carriers or vehicles. Continuous systemic administration of Taurolidine is effective in preventing or reducing tumor metastases to secondary sites following surgical resection of a tumor. Because Taurolidine is associated with few or no adverse side effects and strong antineoplastic effects, it is a safe and potent chemotherapeutic agent for inhibiting colon cancer and preventing metastases.

Taurolidine Inhibits Metastases

The following reagents and procedures were used to evaluate inhibition of tumor cell metastases into liver tissue.

Cell Lines

The human LS-180 cell line was used and maintained in Eagle's minimal essential medium (EMEM, Sigma, St. Louis, Mo.) supplemented with 10% heat-inactivated fetal bovine serum (Sigma, St. Louis, Mo.) and nonessential amino acid (GIBCO) BRL, Grand Island, N.Y.) at 37° C. in a humidified atmosphere of 5% $CO_2$ Animals. Sixty-nine 8-week old nude mice (Harlan Sprague Dawley, Indianapolis, Ind.) were acclimated to a climate and light cycle controlled environment for at least 7 days prior to study. The animals were maintained on a standard laboratory food and water diet ad libitum.

In Vivo Tumor Model

General anesthesia was induced using 400 µl choral hydrate (2%). Using sterile conditions, a vertical paramedian incision was used to expose the spleen. An intrasplenic injection of $1\times10^5$ tumor cells in 0.4 ml of serum free medium was performed, followed by splenectomy using hemoclips for vascular control. The incision was then closed using surgical staples. Beginning post injections days 2 or 5, mice received IP injections of 0.45% normal saline (n=10 per group) or Taurolidine (n=20 per group). Taurolidine (Boehringer Ingelheim, Germany) was given as a daily 0.5 ml IP injection of 2% solution (25 mg/kg) for 5 consecutive days per week for a total of 3 weeks. The day following the last treatment of Taurolidine or 0.45% NS, the mice were sacrificed and examined for gross tumor. Blood was drawn from the right ventricle, immediately centrifuged, and serum collected for CEA assays. The livers were weighed and fixed in HistoFix and representative sections taken for H&E microscopic examination. In addition, 9 mice (n=3 per group) were used to study the tumor model. At days 5, 10 and 15, mice that received a splenic tumor cell injection without any further intervention were sacrificed to assess tumor burden at varying time points. The livers were assessed for gross tumor and submitted in toto for histologic examination.

Cell Proliferation and Viability Assays

Cell proliferation was assessed using a standard MTT (3,(4,5-dimethylthiazol-2yl)2,5-diphenyltetrazolium bromide; Sigma, St. Louis, Mo.) dye at 570 nm. Cells were into seeded in 96-well microtiter plates ($2\times10^5$ cells/well) using 200 µl of medium. After a 12 hour incubation, Taurolidine was applied for a period of 6, 9, 12, 24 or 48 hours. At each time point 20 µl of MTT (5 mg/ml) was added and the cells were incubated at 37° C. for an additional 30 minutes. The medium was removed and the dye was eluted using acidic isopropyl alcohol (0.04N HCl). Cell viability was measured using crystal violet dye. Cells were seeded and treated with Taurolidine as described for the MTT assay. The medium was then removed and the cells were stained and fixed using a crystal violet staining solution containing 0.75% Crystal violet, 50% EtOH, 0.25% NaCl, and 1.75% formaldehyde for 10 minutes at room temperature. After staining and fixation the cells were rinsed with water and air-dried. The crystal violet dye was eluted using a 1% SDS in PBS solution and the absorbance was measured at 540 nm in a microtiter plate reader.

Cytoxicity Assay

Cytotoxicity was quantified using a standard lactate dehydrogenase cytotoxicity assay (Cytotoxicity Detection Kit, Roche). LS-180 cells ($2.5\times10^5$ cell/well) were cultured in Falcon 96-well microtiter plates in a humidified incubator at 37° C., 5% $CO_2$. After 12 hours to allow the cells to become adherent, they were cultured for 12 or 24 hours in complete medium (low control) or medium containing 50, 100, or 400 µm concentrations of Taurolidine. Triton X-100 (1% final concentration) was used to lyse cells and determine the maximum release of LDH enzyme (high control). Cytotoxicity was determined as per the manufacturer's protocol, and the absorbance was measured at 490 nm in a microtiter plate reader.

Cell Cycle Analysis

LS-180 cells were cultured in 100 mm Falcon plates ($5\times10^6$ cells/plate) for 12 hours to become adherent. Cells were incubated for 12, 14 and 48 hours with complete medium (control) or 50, 100 and 400 nm concentrations of Taurolidine. The cells were then treated with 10 µm bromodeoxyuridine (BrdU) for 30 minutes, and both floating and adherent cells were harvested for fixation in 70% ethanol. The DNA was denatured using 2N HCl and labeled with FITC-conjugated anti-BrdU antibody (anti-bromodeoxyuridine-fluorescein monoclonal antibody; Roche, Indianapolis, Ind.). Before analysis by flow cytometry the cells were treated with ribonuclease (Dnase-free ribonuclease, Roche, Indianapolis, Ind.) and propidium iodide (Sigma, St. Louis, Mo.). FACs analysis was performed on a FACscan flow cytometer (Becton Dickinson, N.J.).

Caspase-3 Assay

To measure caspase activity, cells were incubated in six-well Falcon plates ($1\times10^6$ cells/well) and harvested by trypsinization. The cells were then pelleted and lysed as per the manufacturer's recommendation (MBL, Nagoya, Japan) and the cytosolic protein concentration was quantified using a BCA protein assay reagent (Pierce, Rockford, Ill.). The caspase-3 assay was performed in a 96-well microtiter plate using 100 µg of protein and 5 µl of 4 mM DEVD-pNA Substrate (CPP32/caspase-3 Colorimetric Protease Assay Kit; MBL, Nagoya, Japan). The protein and reagent were then incubated for 2 hours at 37° C. A background reading from cell lysates and buffer without DEVD-pNA substrate was subtracted from samples; the assay was performed in triplicate. Samples were read at 405 nm in a microtiter plate reader.

Caspase Inhibition

Caspase Inhibitor I (Z-VAD-fmk; z-Val-Ala-Asp(OMe)-$CH_2F$, Calbiochem; La Jolla, Calif.) was used from a 21 mM stock in DMSO stored at −20° C. until use and then diluted into tissue culture medium immediately prior to its application. After a 2-hour incubation with the caspase inhibitor, cells were treated with Taurolidine. The concentration of caspase inhibitor utilized was optimized by studying the effects of several concentrations of inhibitor and confirmed by demonstrating no change in caspase-3 activity. Untreated cells received an equivalent dilution of DMSO.

Taurolidine Produces Loss of Adherent Cells without Inducing Cell Necrosis or Apoptosis The human LS-180 colon cancer cell line was incubated with 25, 50, 75, and 100 µm concentrations of Taurolidine, and an MTT assay was performed at 6, 9, 12, 24 and 48 hours after Taurolidine administration. An accompanying crystal violet assay was performed under the same conditions. Taurolidine produced a dose dependent decrease in cell number as evident by both assays, producing a 40–50% reduction in cell number after 24 hours using a 100 µm concentrations as shown by FIGS. 1A–B and 2A–B. Treated cells, even at the high concentration of 400 µm, failed to demonstrate cell shrinkage, cytoplasmic condensation, nuclear fragmentation or blebbing when viewed under light microscopy or using the DNA-staining fluorescent dye Hoechst 33258. In addition, flow cytometry using the DNA fluorochrome propidium iodide failed to demonstrate a sub-G1 peak, a finding which when present is suggestive of apoptosis. Flow cytometry was also performed using bromodeoxyuridine (BrdU) to help quantify the proportion of cells in S phase and evaluate cell proliferation. There was no significant change in proliferation or cell cycle between treated and untreated cells as shown in FIGS. 3A–C and FIGS. 4A–D.

Figure 7:
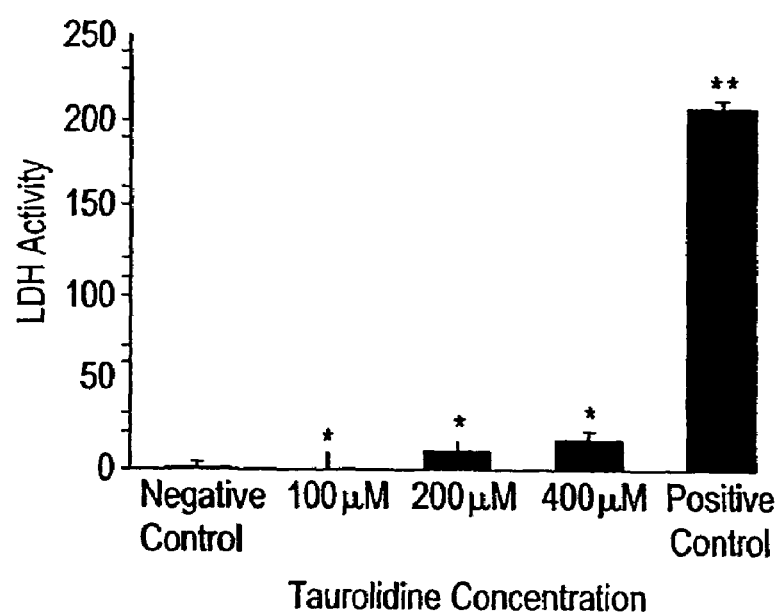
FIG. 7 is a bar graph showing that treatment with Taurolidine produces no significant cytolysis after 24 hours. LS-180 cells were treated with 100, 200, and 400-µM concentrations of Taurolidine and culture medium LDH activity was measured as a means of quantifying plasma membrane damage after 24 hours. Treated cells were compared to untreated cells (low control) and cells lysed with Triton X-100 (high control). Each bar represents mean LDH activity ±SE. *Nonsignificant, Tukey HSD test; **P<0.01, Tukey HSD test.

Cytotoxicity was assessed by measuring lactate dehydrogenase (LDH) activity released from the cytosol of damaged cells. LS-180 cells were exposed to 50, 100 and 400 µm concentrations of Taurolidine and incubated for a period of 12 or 24 hours. Taurolidine, even at a 400 µm concentration, produced minimal cytotoxic effects on LS-180 cells. In all cases the percent cytotoxicity was less than 2% as shown in FIG. 7. These data indicate that Taurolidine causes a decrease in the number of adherent LS-180 cells, evident by a decrease in the MTT and crystal violet assays but does not produce cytolysis or induce apoptosis (FIGS. 1A–B and 2A–B). This is in contradistinction to previously reported in vitro studies of Taurolidine on malignant cell lines.

Taurolidine Inhibits the Development of Hepatic Metastases

Figure 8:
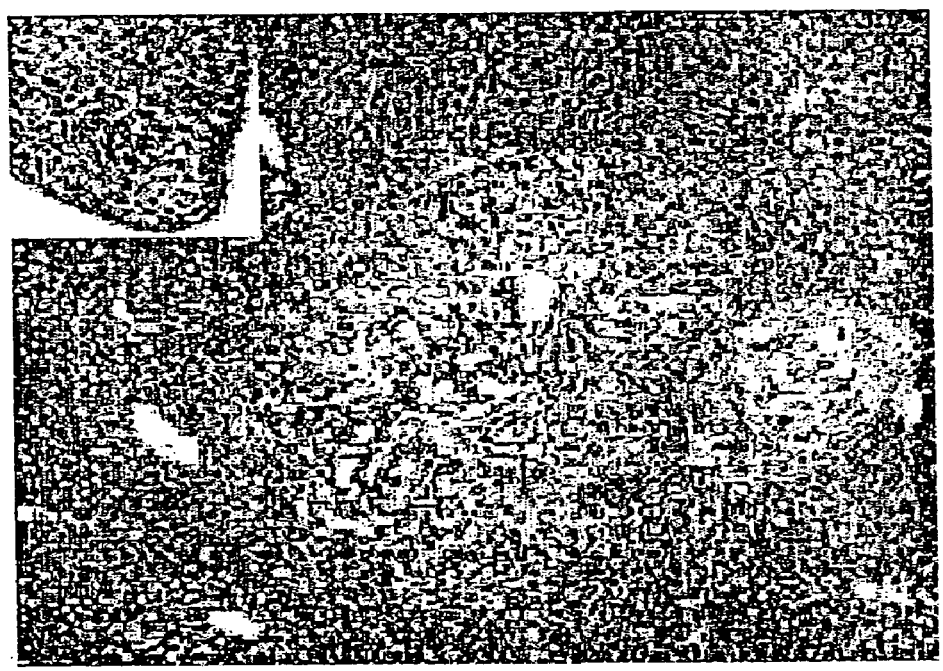
FIG. 8 is a photomicrograph showing that Taurolidine treatment resulted in decreased tumor burden. Photomicrograph of H & E preparations from mouse liver 5 and 10 days after splenic tumor injection with human colon cancer cells (LS-180).
Figure 9A:
FIGS. 9A–D are photographs of liver tissue showing that Taurolidine-treated animals demonstrated a dramatic reduction in hepatic tumor involvement compared to control animals. Tumor burden following saline (control) or Taurolidine treatment. Control (FIG. 9A) and Taurolidine-treated (FIG. 9B) mice beginning treatment 2 days after splenic tumor injection with LS-180 cells. Control (FIG. 9C) and Taurolidine-treated (FIG. 9D) mice beginning treatment 5 days after splenic tumor injection.
Figure 9B:
Figure 9C:
Figure 9D:

In order to study tumor development in our liver metastases model, mice received no further intervention after tumor injection at three time points. At 5 and 10 days following splenic injection, no tumor was observed grossly, but small foci of tumor were demonstrated in H & E preparations using light microscopy as shown in FIG. 8. By day 15 gross tumor was observed as small firm punctate lesions on the liver surface and within the liver parenchyma on cross section (FIG. 8).

Figure 11:
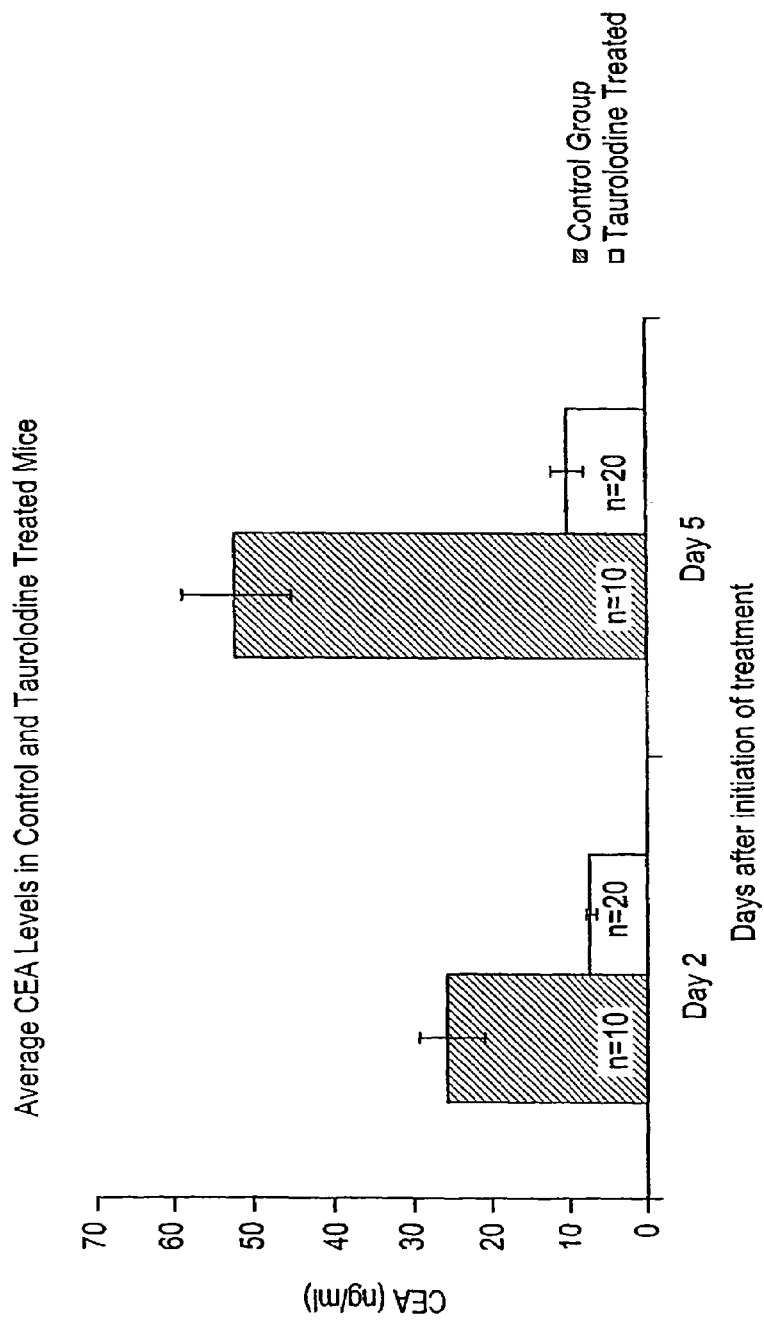
FIG. 11 is a bar graph showing serum carcinoembryonic antigen levels in control and Taurolidine treated animals. The treated animals demonstrated a 69% and 78% reduction in serum CEA levels in the 2 and 5 day groups respectively after 3 weeks of therapy. The decreased CEA is representative of decreased tumor burden in Taurolidine treated animals.

In the Taurolidine and control study groups all mice tolerated the full 3-week course of treatment. On gross inspection there was a marked reduction in tumor burden in animals treated with Taurolidine compared to controls (FIGS. 6A–D), although there were no controls completely free of tumors. The group beginning treatment 5 days following tumor injection, compared to the group starting treatment after 2 days, had greater tumor burden in both the treated and control groups. These findings were supported by measurement of both liver weights and serum CEA levels. There was an 18% reduction in liver weight for the group beginning Taurolidine treatment after 2 days and a 22% reduction for the group beginning treatment after 5 days from splenic tumor injection (FIG. 10). In addition, the LS-180 cells are known to express CEA, and the Taurolidine treated animals demonstrated a 69% reduction in serum CEA levels in the 2 day group and a 78% reduction of serum CEA in the 5 day group compared to the control animals (FIG. 11 and Table 1).

TABLE 1

| | Serum CEA (ng/ml) | |
|---|---|---|
| | Day 2 | Day 5 |
| Untreated Control Group (n = 10) | 25.20 ± 4.24 (P < 0.01) | 53.58 ± 6.77 (P < 0.01) |
| Taurolidine Treatment Group (n = 20) | 7.73 ± 0.52 (P < 0.01) | 11.88 ± 1.97 (P < 0.01) |

Table 1 shows the effect of Taurolidine treatment on serum CEA levels. Serum CEA levels after completing Taurolidine treatment were compared to untreated controls receiving saline. Mice treated with Taurolidine demonstrated a 69% (P<0.01) reduction in CEA levels in the group beginning treatment 2 days after splenic injection, and a 78% (P<0.01) reduction in the group beginning treatment after 5 days. The CEA level from the serum of 3 normal nude mice was undetectable and served as a negative control. The data are represented as mean serum CEA level ±SE. *P<0.01 by Tukey HSD test Although Taurolidine has been used as an antibiotic, particularly in cases of severe peritonitis where it is used as a peritoneal lavage, it has recently found a role as a putative antineoplastic agent. The use of Taurolidine as a local or systemic agent for established hepatic metastases from a human colon cancer cell line was studied. In the animal model described herein, splenic injection of tumor cells was used to seed the liver via the portal system. Established metastases was histigically demonstrated as early as 5 days post injection. Grossly, tumor could be appreciated as small punctate nodules within the liver parenchyma after 15 days. After 24 days, in some cases, the liver had been almost completely replaced by tumor. Using a Taurolidine regimen of daily IP injections, a marked decrease in tumor burden was demonstrated compared to control animals. This was observed in animals beginning treatment after both 2 and 5 days post splenic tumor injection but was more pronounced in the latter group, producing a 78% reduction in CEA levels compared to control animals. These findings indicated that Taurolidine strikingly inhibits the development and progression of established liver metastases.

The data support a role for Taurolidine alone or in combination with other chemotherapeutic agents for antineoplastic therapy. A 60% decrease in adherent tumor cells was shown in MTT and crystal violet assays; the decrease occurred in a dose-dependent manner with significant effects observed after only 9 hours of treatment. Unlike earlier reports, Taurolidine was not found to induce apoptosis or cytolysis in the LS-180 cell line. Instead, it appeared that the decreased number of cells after treatment with Taurolidine was secondary to loss of cell adherence. There were a decreased number of adherent cells after only 9 hours of drug exposure, but there was no evidence of cytotoxicity or apoptosis.

Taurolidine and Tumor Cell Adherence

Taurolidine inhibits tumor cell adherence. Normal epithelial cells critically depend upon cell-matrix interaction for cell survival, and without this interaction they undergo a form of apoptosis termed anoikis. Certain malignant epithelial cells differ in this respect; they possess a reduced sensitivity to anoikis, allowing them to survive in the absence of matrix attachment, facilitating the formation of distant metastases. This phenomenon provides an explanation as to why in some cell lines Taurolidine produces apoptosis, and in the LS-180 cells it produces only loss of cell adherence; different cell lines have varied sensitivity to anchorage loss and anoikis. The action of Taurolidine may depend directly upon a decrease in cell adherence.

The liver remains the most common site of colorectal metastases, and the 5-year survival rate remains between 24 and 46% for treated patients. The data described herein indicate that Taurolidine is an effective chemotherapeutic agent for the prevention of metastases into the liver and for the treatment of established hepatic metastases from such primary tumors as colon cancer. Intraperitoneal, intravenous, and local injection to preferentially target the liver are useful to combat metastatic disease. Taurolidine is also used to treating tumor metastases elsewhere in the body. Because of its very low toxicity and dramatic antineoplastic effects, Taurolidine is a safe and powerful agent to prevent and inhibit tumor metastases.

Other embodiments are within the following claims.

What is claimed is:

1. A method of inhibiting the development of metastases of a primary tumor to a tissue of a liver in an individual after excision of the primary tumor, comprising directly contacting said tissue with taurolidine isolating said liver from systemic circulation.

2. The method of claim 1, wherein said primary tumor is not a liver tumor.

3. The method of claim 1, wherein said primary tumor is in an organ of the peritoneal cavity.

4. The method of claim 1, wherein said individual is identified as being at risk of developing a metastatic liver tumor.

5. The method of claim 1, wherein said individual is a mammal.

6. The method of claim 5, wherein said mammal is a human.

7. The method of claim 1, wherein said individual is identified as suffering from a colorectal tumor.

8. The method of claim 1, wherein said individual is identified as suffering from a tumor selected from the group consisting of a lung tumor, breast tumor, kidney tumor, colon tumor, esophageal tumor, testicular tumor, pancreatic tumor, melanoma, and choriocarcinoma.

9. The method of claim 1, wherein said taurolidine is administered to said liver by perfusion in a direction of naturally-occurring blood flow.

10. The method of claim 1, wherein said liver is perfused with said taurolidine in situ.

11. The method of claim 1, wherein said taurolidine is administered to said liver by retrograde perfusion.

12. The method of claim 9, wherein said perfusion is carried out in conjunction with an abdominal surgery.

13. The method of claim 1, wherein said Taurolidine is administered by in-dwelling catheter.

14. The method of claim 1, wherein said Taurolidine is administered at a dose which increased caspase activity in a cell.

15. The method of claim 1, wherein said Taurolidine is administered intravenously.

16. The method of claim 11, wherein said perfusion is carried out in conjunction with an abdominal surgery.

* * * * *